(12) United States Patent
Stefik et al.

(10) Patent No.: US 11,555,815 B2
(45) Date of Patent: Jan. 17, 2023

(54) DETECTION OF MOLECULE-NANOPARTICLE INTERACTIONS WITH LIGAND SHELLS

(71) Applicant: University of South Carolina, Columbia, SC (US)

(72) Inventors: Morgan Stefik, Columbia, SC (US); Zachary Marsh, Columbia, SC (US)

(73) Assignee: UNIVERSITY OF SOUTH CAROLINA, Columbia, SC (US)

( * ) Notice: Subject to any disclaimer, the term of this patent is extended or adjusted under 35 U.S.C. 154(b) by 377 days.

(21) Appl. No.: 16/784,317

(22) Filed: Feb. 7, 2020

(65) Prior Publication Data

US 2020/0256865 A1 Aug. 13, 2020

Related U.S. Application Data

(60) Provisional application No. 62/802,358, filed on Feb. 7, 2019.

(51) Int. Cl.
| | |
|---|---|
| *G01N 1/22* | (2006.01) |
| *B82Y 30/00* | (2011.01) |
| *G01N 33/543* | (2006.01) |
| *G01N 24/08* | (2006.01) |
| *B82Y 15/00* | (2011.01) |
| *B82Y 40/00* | (2011.01) |

(52) U.S. Cl.
CPC ......... *G01N 33/54346* (2013.01); *G01N 1/22* (2013.01); *G01N 24/088* (2013.01); *B82Y 15/00* (2013.01); *B82Y 30/00* (2013.01); *B82Y 40/00* (2013.01)

(58) Field of Classification Search
CPC .. G01N 1/22; G01N 24/088; G01N 33/54346; B82Y 30/00
See application file for complete search history.

(56) References Cited

PUBLICATIONS

M. Kimura et al., Volatile Organic Compound Sensing by Gold Nanoparticles Capped with Calix[4]arene Ligand, 40 Chem. Lett. 1402-1404 (2011).*
K. K. Kartha et al., A Carbazole-Fluorene Molecular Hybrid for Quantitative Detection of TNT Using a Combined Fluorescence and Quartz Crystal Microbalance Method, 16 Phys. Chem. Chem. Phys. 18896-18901 (2014).*
Z. M. Marsh et al., QCM Detection of Molecule-Nanoparticle Interactions for Ligand Shells of Varying Morphology, 10 Nanoscale 19107-19116 (2018).*

* cited by examiner

*Primary Examiner* — Randy Boyer
(74) *Attorney, Agent, or Firm* — Burr & Forman LLP; Douglas L. Lineberry

(57) ABSTRACT

A quartz crystal microbalance coated with functionalized nanoparticles used to detect molecule-nanoparticle interactions to assist with characterization of difficult to predict molecule-nanoparticle interactions for novel ligand chemistries and, particularly, mixed ligand nanoparticles exhibiting different ligand morphologies, in order to quantify nanoparticle-molecule interactions independently from more complex solvation requirements.

15 Claims, 21 Drawing Sheets

Table S1. NP diameter and distribution results from the Porod fitting results

| NP Batch | Average NP Diameter (nm) | Standard Deviation (nm) |
|---|---|---|
| Am. | 1.7 | 0.4 |
| 0F | 1.8 | 0.4 |
| 25F | 1.6 | 0.5 |
| 52F | 2.0 | 0.4 |
| 100F | 1.8 | 0.6 |

FIGURE 11

Table S2. Ligand shell compositions and surface densities for mixed nanoparticles.

| NP Batch | Exchange Solution Composition (mol% PFOT) | Ligand Shell Composition (mol% PFOT) | NP Concentration UV-Vis (M$\times 10^{-6}$) | Ligand Concentration NMR (M$\times 10^{-4}$) | Ligand Surface Density, σ (#/nm$^2$) |
|---|---|---|---|---|---|
| 0F | 0 | 0 | 2.6 | 1.2 | 5.2 |
| 20F | 25 | 20 | 0.92 | 0.45 | 1.2 |
| 31F | 40 | 31 | 2.8 | 3.7 | 3.7 |
| 39F | 30 | 39 | 1.9 | 0.92 | 1.5 |
| 52F | 45 | 52 | 2.3 | 0.59 | 1.0 |
| 59F | 50 | 59 | 2.1 | 0.41 | 1.2 |
| 73F | 75 | 73 | 1.4 | 0.19 | 2.5 |
| 93F | 80 | 93 | 1.5 | 0.22 | 4.0 |
| 100F | 98 | 100 | 1.7 | 3.7 | 4.1 |

FIGURE 12

Table S1.

| NP Batch | CF$_3$ Shift (ppm) | 7$^{th}$ CF$_2$ (ppm) |
|---|---|---|
| 0F | - | - |
| 20F | -82.00 | -126.78 |
| 31F | -82.07 | -127.05 |
| 39F | -82.09 | -127.08 |
| 52F | -82.32 | -127.18 |
| 59F | -82.33 | -127.20 |
| 73F | -82.59 | -127.25 |
| 93F | -82.52 | -127.54 |
| 100F | -82.54 | -127.54 |

FIGURE 21

DETECTION OF MOLECULE-NANOPARTICLE INTERACTIONS WITH LIGAND SHELLS

BACKGROUND OF THE INVENTION

1) Field of the Invention

The present invention relates to a quartz crystal microbalance (QCM) approach to more broadly quantify molecule-NP interactions via vapor phase uptake into solid NP-films independent from solvation constraints.

2) Description of Related Art

Nanoparticles (NPs) have gained widespread interest for a wide array of applications such as chemical and biological sensing, drug delivery for nanomedicine, self-assembly, and removal of contaminants. The performance of a NP for an application is largely influenced by its intermolecular interactions with the local environment as determined by the character of the ligand shell. The ligand shell is the ultimate interface of the NP with the outside world and thus governs interactions with other objects. The properties affected by the ligand shell thus range from solubility, to self-assembly, drug delivery, biocompatibility, and targeted molecular uptake. Mixtures of ligands have been shown to enable hybrid behaviors, e.g., NPs with extensive hydrophobic or fluorine content can exhibit solubility in water and other aqueous media.

The morphology of mixed ligand shells also significantly modifies NP behavior. On flat substrates, ligand mixtures phase separate to reduce the enthalpic interfacial area where the surface tension has a monotonic dependence on the ensemble composition. Here, the nearest-neighbor molecular environment within each phase is identical to the mono-ligand film.

In other words, ligands phase separated over sufficient distance will interact independently with the external environment. Janus NPs are analogously phase separated with ligand domains on opposite sides of each NP. Janus NPs thus exhibit a monotonic continuum of behavior principally corresponding to the ensemble of two mono-ligand environments. Due to high curvature, mixed ligand NPs can also exhibit patchy and stripe-like ligand morphologies when coupled with appropriate pairs of ligands having different length. The lowest free-energy configuration can promote mixed ligand interfaces to increase conformational entropy of the longer ligand. Here the longer ligands explore additional conformational space when proximal to the shorter ligands.

This remarkable entropy-driven ordering is widely documented to occur under specific conditions. Patchy and stripe-like ligand morphologies have small <2 nm ligand domains that are dominated by the mixed-ligand interface. Patchy and stripe-like NPs can thus exhibit non-monotonic trends in behavior where the local molecular environment behaves distinctly from the bulk ensemble. This follows naturally with the increasing contribution of dissimilar nearest-neighbor ligands where their interface behaves differently from either ligand alone. The changes in molecule-NP interactions are not yet predictable a priori and are tedious to measure where each molecule-NP interaction is tested individually, typically with a solubility limit measurement. The non-monotonic behavior exhibited by patchy and stripe-like nanoparticles has been explained by a combination of cavitation suppressing selective-solvent uptake or by confinement enhancing solvent uptake into appropriately matched molecular environments. Cavitation and confinement thus work in opposing directions where the balance between the two leads to variable non-monotonic molecule-NP behaviors. For example, a recent report with mixed ligand amphiphilic NPs having 67% hydrophobic ligand were most soluble in polar alcohols and this alcohol solubility was reduced when increasing the hydrophilic ligand content.

NP saturation experiments with different solvents or solvation conditions are widely used to quantify solvent-NP interactions. In contrast, more general measurements of molecule-NP interactions do not necessarily require a solvation shell. For example, NP drug loading is a separate criterion from solvation in the delivery medium.

Accordingly, it is an object of the present invention to provide a method for detecting the interaction of molecules with nanoparticles of diverse surface chemistries in order to assist with characterization of difficult to predict molecule-nanoparticle interactions for novel ligand chemistries and, particularly, mixed ligand nanoparticles exhibiting different ligand morphologies, in order to quantify nanoparticle-molecule interactions independently from more complex solvation requirements.

SUMMARY OF THE INVENTION

The above objectives are accomplished according to the present invention by providing in a first embodiment a quartz crystal microbalance method for detecting molecular interactions with nanoparticles to predict molecule-nanoparticle interactions comprising. The method may include preparing a nanoparticle film on a quartz crystal, exposing the nanoparticle film to at least one molecular vapor; and quantifying mass uptake via analyzing a resonant frequency of the quartz crystal. Further, the method may include correlating nonmonotonic uptake trends to ligand shell morphologies as a function of confinement and cavitation effects. Still further, non-solvents may be used to quantify molecular/nanoparticle interactions. Yet still, determining morphology of at least one molecule/nanoparticle shell may be accomplished via analyzing nuclear magnetic resonance chemical shifts. Again, interfaces of different ligands have a different chemical shift wherein extent of chemical shift may be a weighted average of at least one local ligand environment. Still again, molecular uptake may be measured without requiring a solvation sphere. Further again, the nanoparticle film may be formed by spin coating. Still yet, the method may include comparing molecular mass uptake to nanoparticle film mass to quantify extent of uptake. Again, the method may include probing for non-monotonic trends in molecule-nanoparticle interactions with changes to ligand composition. Still further, the method may include eliminating nanoparticle size distribution as a variable via employing ligand exchange.

In an alternative embodiment, the current disclosure provides a method to quantify mixed ligand shell molecule-nanoparticle interaction. The method may include measuring vapor phase uptake of molecules into a solid nanoparticle film, deposited on a crystal, via nuclear magnetic resonance, wherein the nanoparticle film comprises mixed ligand nanoparticles with constant size and variable composition; and the method is independent of solvation criteria. Further, the crystal may be quartz. Still further, patchy ligand morphologies may exhibit more molecule uptake than either stripe-like or mono-ligand nanoparticles. Yet again, measurements may be taken without requiring a solvation shell. Further still, ligand stripping may be employed. Yet further, the method may include eliminating nanoparticle size distribution as a variable via employing ligand exchange.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

FIG. 11 shows table S1 displaying NP diameter and distribution results from Porod fitting results.

FIG. 12 shows table S2 displaying ligand shell compositions and surface densities for mixed nanoparticles.

FIG. 21 shows $^{19}F$ NMR shift results for the —CF$_3$ and 7th CF$_2$ unit of the PFOT ligand.

Figure 1:
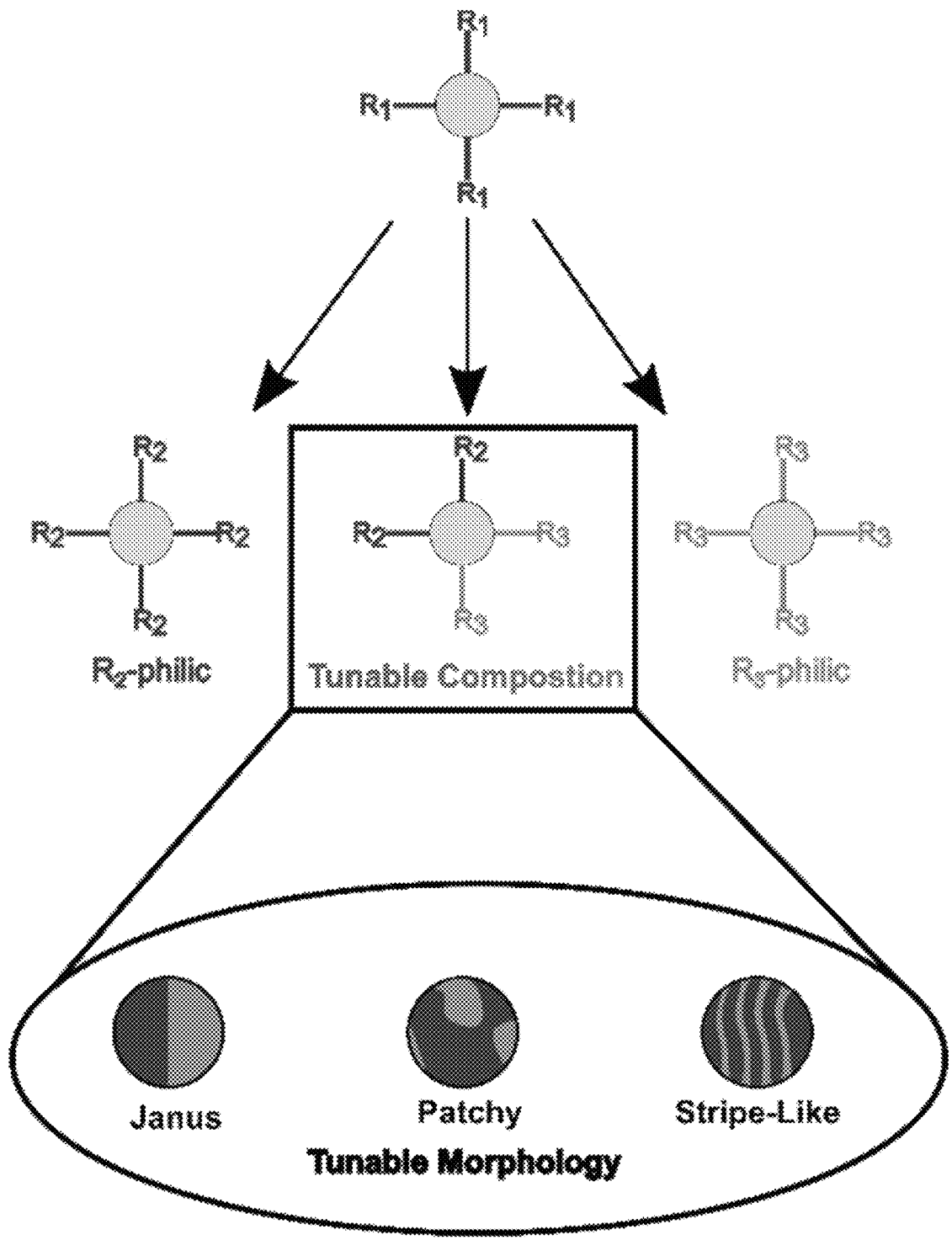
FIG. 1 shows NPs with mixed ligand shells can have variable composition and ligand morphology.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF A PREFERRED EMBODIMENT

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

The current disclosure provides a quartz crystal microbalance (QCM) approach to more broadly quantify molecule-NP interactions via vapor phase uptake into solid NP-films independent from solvation constraints. The composition and morphology of mixed ligand shells were found to exhibit pronounced non-monotonic behavior that deviated from continuum thermodynamics, highlighting the influence of ligand morphology upon absorption/adsorption. Alkyl and perfluorinated thiols were used as a model case with constant core-size distribution. The ligand morphology was determined by 19F NMR. Molecule uptake into NPs was measured with five benzene derivatives with varied degree of fluorination. For the cases examined, QCM measurements revealed enhanced uptake for patchy morphologies and suppressed uptake for stripe-like morphologies. These results contrast with insights from solubility measurements alone where QCM sometimes identified significant molecular uptake with poor solvents. This QCM method thus provides new insights to molecule-NP interactions independent of the solvation shell.

The current disclosure has developed a quartz crystal microbalance (QCM) method to quantify molecule-NP interactions via vapor phase uptake into solid NP thin films. QCM has previously been used on NP films to monitor chemiresistence, detect various biomaterials, and to analyze cellular interactions due to its high sensitivity. The approach uses miniscule NP quantities and can uniquely quantify molecule-NP interactions with non-solvents. In one embodiment, the current disclosure examines a model system consisting of 1.8 nm gold NPs with a variable combination of short fluorophilic ligands and long lipophilic ligands that were expected to form patchy and stripe-like ligand morphologies. The molecule-NP interactions were examined for a systematic series of fluorinated benzene derivatives as a function of NP ligand composition and morphology. Non-monotonic trends in solvent uptake were correlated to the ligand shell morphologies as a function of confinement and cavitation effects.

Results and Discussion: Preparation of Mixed-Ligand NP

A range of mixed ligand NPs were synthesized under conditions expected to form patchy and stripe-like ligand morphologies. The general requirements for these morphologies are a combination of ligands with different lengths on a NP of suitable curvature, e.g. generally ~2-8 nm in diameter. A recent experimental and computational study examined mixtures of fluorophilic and lipophilic ligands on 2-4 nm gold NPs where the length of the ligands were varied across a wide composition range to determine the impact on ligand morphology. Janus regions were observed if the ligands had similar length. The flexible lipophilic ligands needed to be >4-6 carbons longer than the stiff fluorinated ligands to form patchy or stripe-like morphologies. The morphologies were mapped for patchy (0-30 mol % fluorinated and 60-100 mol % fluorinated) and stripe-like (30-60 mol % fluorinated) morphologies. Prior work suggests that the current disclosure's selection of DDT and PFOT (4 carbon difference) with 1.8 nm diameter Au NPs will yield patchy and stripe-like ligand morphologies.

Mixed ligand NPs were prepared using standard methods. See, Hostetler, M. J.; Green, S. J.; Stokes, J. J.; Murray, R. W. Monolayers in Three Dimensions: Synthesis and Electrochemistry of ω-Functionalized Alkanethiolate-Stabilized Gold Cluster Compounds. *J. Am. Chem. Soc.* 1996, 118, 4212-4213, which is hereby incorporated by reference. Murray et. al developed a method for mixed ligand NPs using a post-synthesis ligand exchange. This process was later expanded to displace weakly bound amine or phosphorous ligands with stronger binding thiol ligands. See Brown, L. O.; Hutchison, J. E. Convenient Preparation of Stable, Narrow-Dispersity, Gold Nanocrystals by Ligand Exchange Reactions. *J. Am. Chem. Soc.* 1997, 119, 12384-12385, which is hereby incorporated by reference. The NP core size is thus constant and is decoupled from the final ligand chemistry, see FIG. 1. FIG. 1 shows that NPs with mixed ligand shells can have variable composition and ligand morphology. Displacement of weakly bound ligands (R1) with strong binding ligands (R2, R3) yields systematic NP series with constant NP core size distribution and variable ligand shells.

Figure 2:
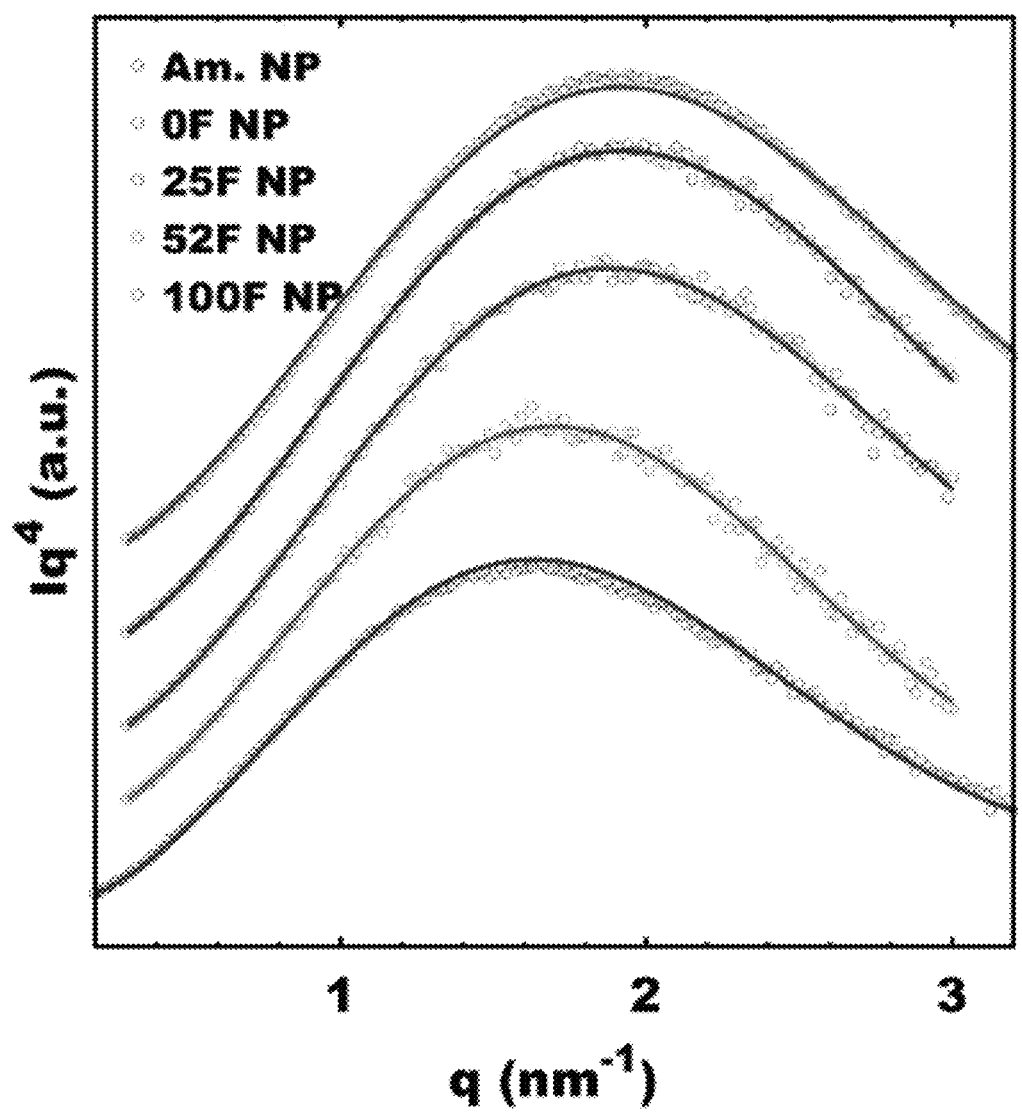
FIG. 2 illustrates Porod plots of aminated, 0F, 25F, 52F, 100F NP solutions.

Our synthesis used a procedure for aminated <5 nm Au NPs followed by amine displacement with lipophilic DDT and fluorophilic PFOT ligands. See Jana, N. R.; Peng, X. Single-Phase and Gram-Scale Routes toward Nearly Monodisperse Au and Other Noble Metal Nanocrystals. *J. Am. Chem. Soc.* 2003, 125, 14280-14281, which is hereby incorporated by reference. The NP behavior followed broad expectations where PFOT-rich NPs precipitated from toluene whereas DDT-rich NPs were toluene soluble. SAXS was used to confirm the NP size distributions. Comparison of the Am. NPs to ligand displaced NPs resulted in similar scattering curves with the nearly identical q-positions for local minima and maxima, see FIG. 2. (FIG. 2 illustrates Porod plots of aminated, 0F, 25F, 52F, 100F NP solutions. Data points and best-fit lines are indicated. Scattering data are offset vertically for clarity.) Each dataset was well fitted using a hard sphere form factor with a Gaussian size distribution. The results indicated 1.6-2.0±0.4-0.6 nm NP diameter distribution, with some minor differences between the converged fits (see FIG. 11, Table S1). Thus, ligand displacement was shown to not significantly alter the NP core size distribution.

Figure 3:
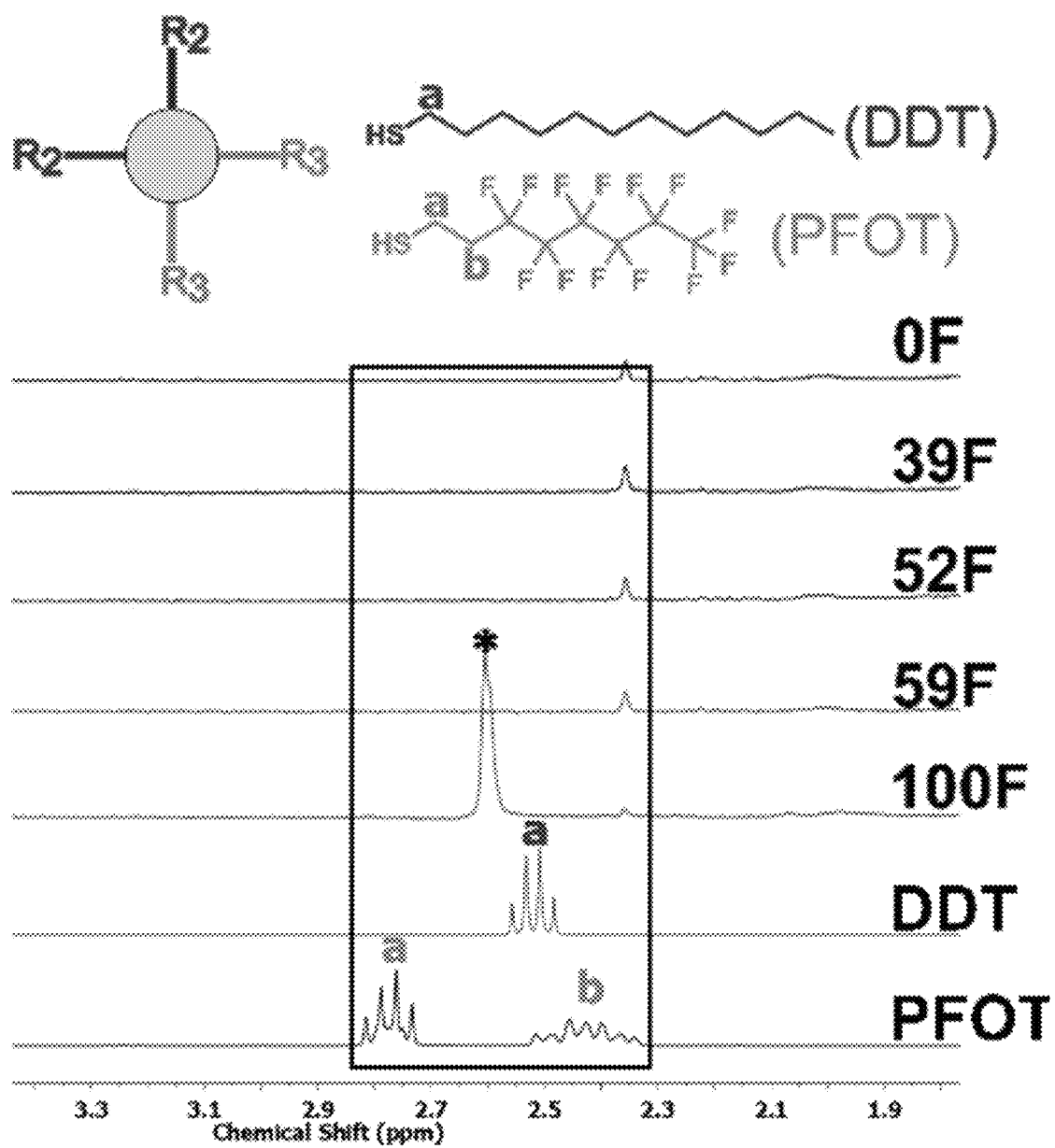
FIG. 3 shows NMR of the ligated nanoparticles after washing showing the absence of free ligand.
Figure 4:
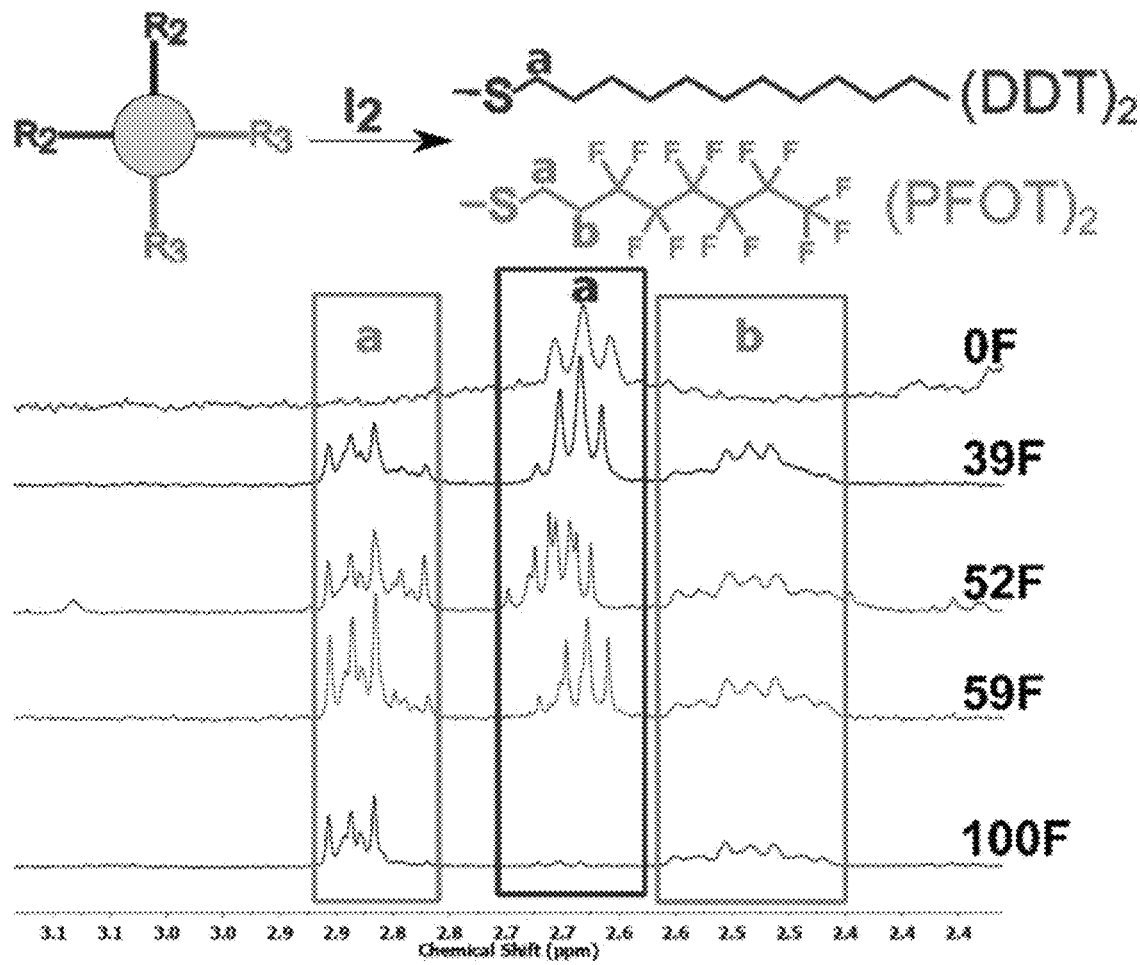
FIG. 4 shows NP bound ligand composition measured by NMR after ligand stripping with iodine, resulting in the corresponding disulfide mixtures
Figure 5:
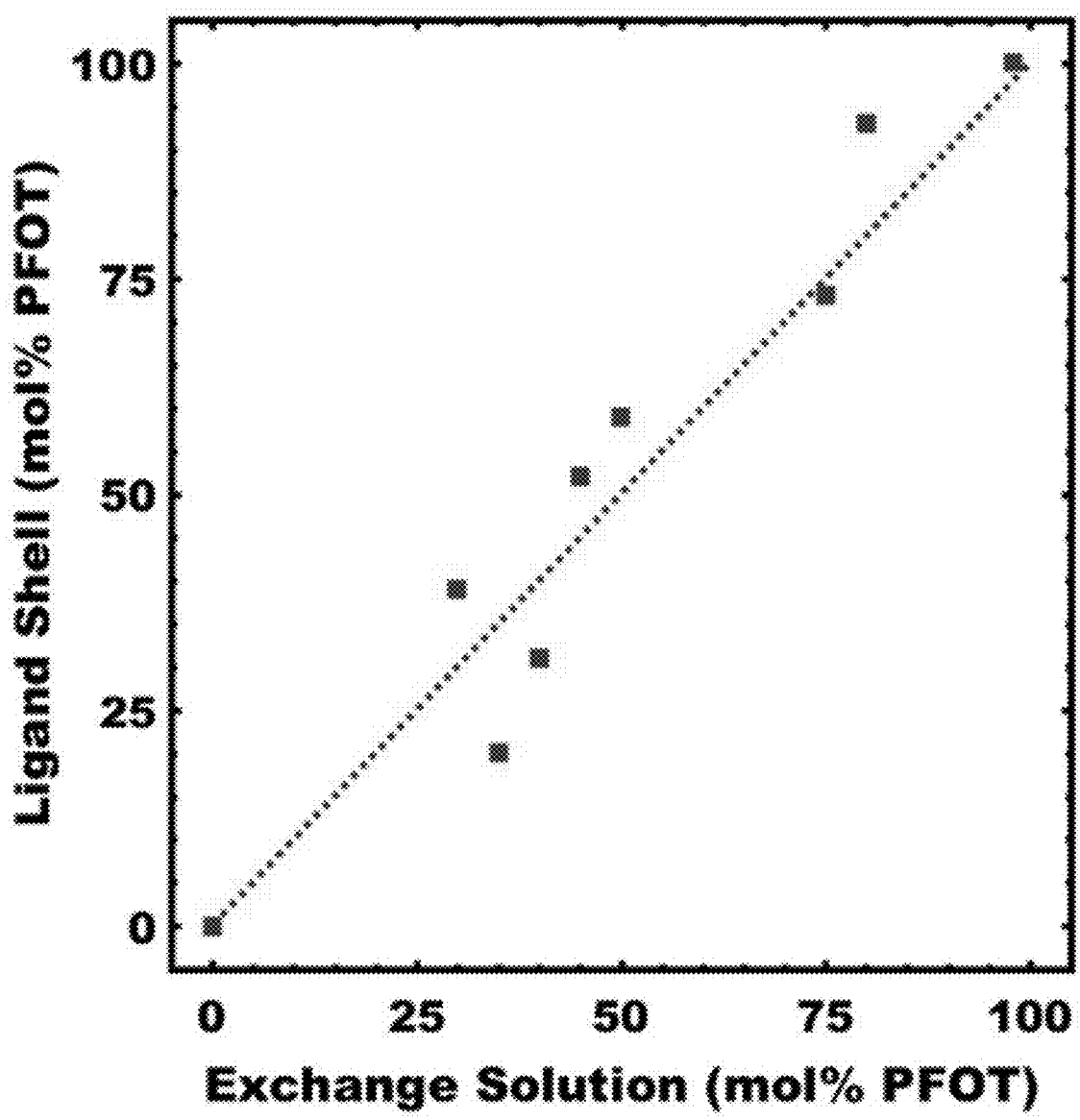
FIG. 5 shows correlation of ligand exchange solution composition to the composition of bound ligands on nanoparticle surfaces (DDT and PFOT ligands).

The resulting mixed ligand NPs were rigorously purified before determination of the ligand surface density and composition. The synthesis solution contained a surfactant to improve NP solubility however residual surfactant would influence subsequent measurements of molecule-NP interactions. The NPs were thus purified with iterative dispersal/precipitation cycles. The solubility of the NPs changed markedly with the cleaning steps as well documented before in Dass, A.; Guo, R.; Tracy, J. B.; Balasubramanian, R.; Douglas, A. D.; Murray, R. W. Gold Nanoparticles with Perfluorothiolate Ligands. Langmuir 2008, 24, 310-315 and Yonezawa, T.; Onoue, S. Y.; Kimizuka, N. Self-Organized Superstructures of Fluorocarbon-Stabilized Silver Nanoparticles. Adv. Mater. 2001, 13, 140-142, both of which are hereby incorporated by reference. NMR spectra after six wash cycles were without sharp peaks associated with free-ligand or surfactant, see FIG. 3. (FIG. 3 provides NMR of the ligated nanoparticles after washing showing the absence of free ligand. NMR of the DDT thiol is represented by the red a while the free PFOT is denoted at the bottom of the image. *TFT added for solubility. The NPs were named by the mol % of PFOT in the DT/PFOT ligand shells, see FIG. 4.) An aliquot of the mixed ligand NPs was then striped of ligands using metallic iodine to improve quantification of the formerly-bound ligand population, see FIG. 4. (FIG. 4 shows the NP bound ligand composition measured by NMR after ligand stripping with iodine, resulting in the corresponding disulfide mixtures.) The ratio of bound ligands was fully tunable from 0-100 mol % PFOT and with small deviation from the exchange solution, see FIG. 5 and FIG. 12 showing Table S2, which shows ligand shell compositions and surface densities for mixed nanoparticles. (FIG. 5 shows correlation of ligand exchange solution composition to the composition of bound ligands on nanoparticle surfaces (DDT and PFOT ligands)). A non-convoluted internal standard (1,4-difluorobenzene) was included in the same ligand stripping experiments to determine the ligand surface concentration. A fringe benefit of the chosen internal standard is that it also improves NP solubility. Comparison of the ligand concentration to the NP concentration determined by optical absorption experiments yielded the surface ligand density. The ligand surface density for all mixed-ligand NPs examined were within the range of 1-5 #/nm$^2$, consistent with similar reports of NPs without detectable free-ligand, see FIG. 12, Table S2). A series of purified DDT/PFOT mixed ligand NPs were thus prepared with constant size distribution.

Determination of Ligand Morphology by $^{19}$F NMR

Numerous methods can determine the morphology of mixed ligand NP shells. Common methods include NMR, mass spectroscopy, Scanning Tunneling Microscopy, MALDI-TOF, UV-Vis paired with Cryo-TEM, Electron Spin Resonance, Infrared Spectroscopy paired with STM, and contact angle measurements. The current disclosure used the method developed by Pasquato et. al to determine the mixed ligand morphology using trends in $^{19}$F NMR chemical shifts. See Sologan, M.; Marson, D.; Polizzi, S.; Pengo, P.; Boccardo, S.; Pricl, S.; Posocco, P.; Pasquato, L. Patchy and Janus Nanoparticles by Self-Organization of Mixtures of Fluorinated and Hydrogenated Alkanethiolates on the Surface of a Gold Core. ACS Nano 2016, 10, 9316-9325, which is hereby incorporated by reference. The method was demonstrated with similar fluorophilic/lipophilic ligand mixtures and was supported by computational predictions.

By using $^{19}$F NMR, which has a high sensitivity due to the large chemical shift range, small changes in the local environment result in larger chemical shifts. If a ligand is surrounded by identical neighbors, similar to a mono-ligand film, then the chemical shift is insensitive to composition changes. Interfaces of different ligands have a different chemical shift where the extent of the shift is a weighted average of the local ligand environments. Distinct trends in chemical shift with ligand composition are anticipated for different sequences of ligand morphologies. Linear decays, exponential decays, and sigmoidal decays were previously correlated to random packing, patchy/Janus, and patchy/stripe-like morphologies, respectively.

Figure 6:
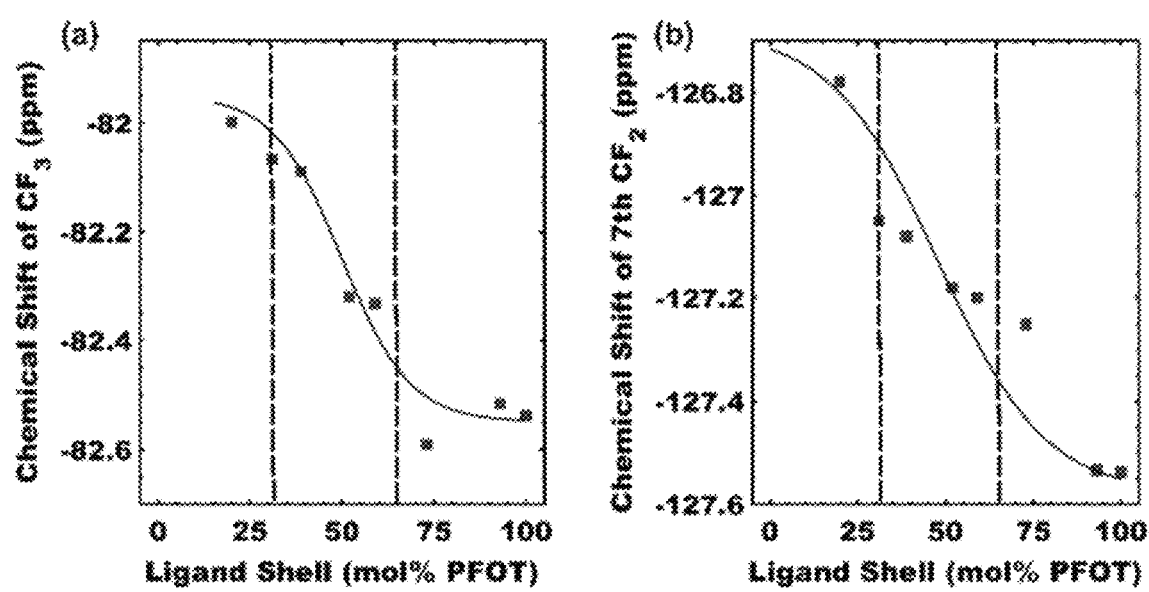
FIG. 6 shows trends of $^{19}F$ NMR chemical shift for —CF3 (a) and the 7th —CF2- (b) on PFOT as a function of NP ligand composition (DDT/PFOT).

The $^{19}$F NMR measurements of both the CF$_3$ group centered near ~80 ppm and the CF$_2$ group centered near ~127 ppm both exhibited sigmoidal trends in chemical shift with ligand composition for the synthesized NP series, see FIG. 6. (FIG. 6 shows trends of $^{19}$F NMR chemical shift for —CF$_3$ (a) and the 7th —CF$_2$- (b) on PFOT as a function of NP ligand composition (DDT/PFOT). A sigmoidal guide line is presented. Interpreted transitions in ligand morphology are indicated with dashed drop lines.). Both curves exhibit similar trends in the chemical shift decay suggesting transition from patchy to stripe-like to patchy morphologies, similar to analogous NP preparations.

QCM Quantification of Molecule-NP Interactions

A custom QCM apparatus was constructed to quantify molecule-NP interactions. Each NP-film was prepared directly on a quartz crystal by spin coating NP solutions. The NP-film was subsequently exposed to solvent vapor and the mass uptake was quantified by the shifting resonant frequency of the quartz crystal. An advantage of QCM is rapid real time feedback with high mass-resolution, the use of minute NP quantities, and the ability to measure molecule uptake without requiring a solvation sphere. Early experiments guided selection of films that were approximately 60 nm thick or less to minimize diffusion time. This thickness was consistently achieved by using a 1 wt % NP solution and a spin speed of 5,000 rpm for an even thin film on the crystal surface. Slower spin speeds (<2,000 rpm) resulted in >100 nm thick films with excessive equilibration times. For typical experiments, the frequency response to vapor was exponential with a time constant that ranged for each film from 8-14 minutes.

Figure 7:
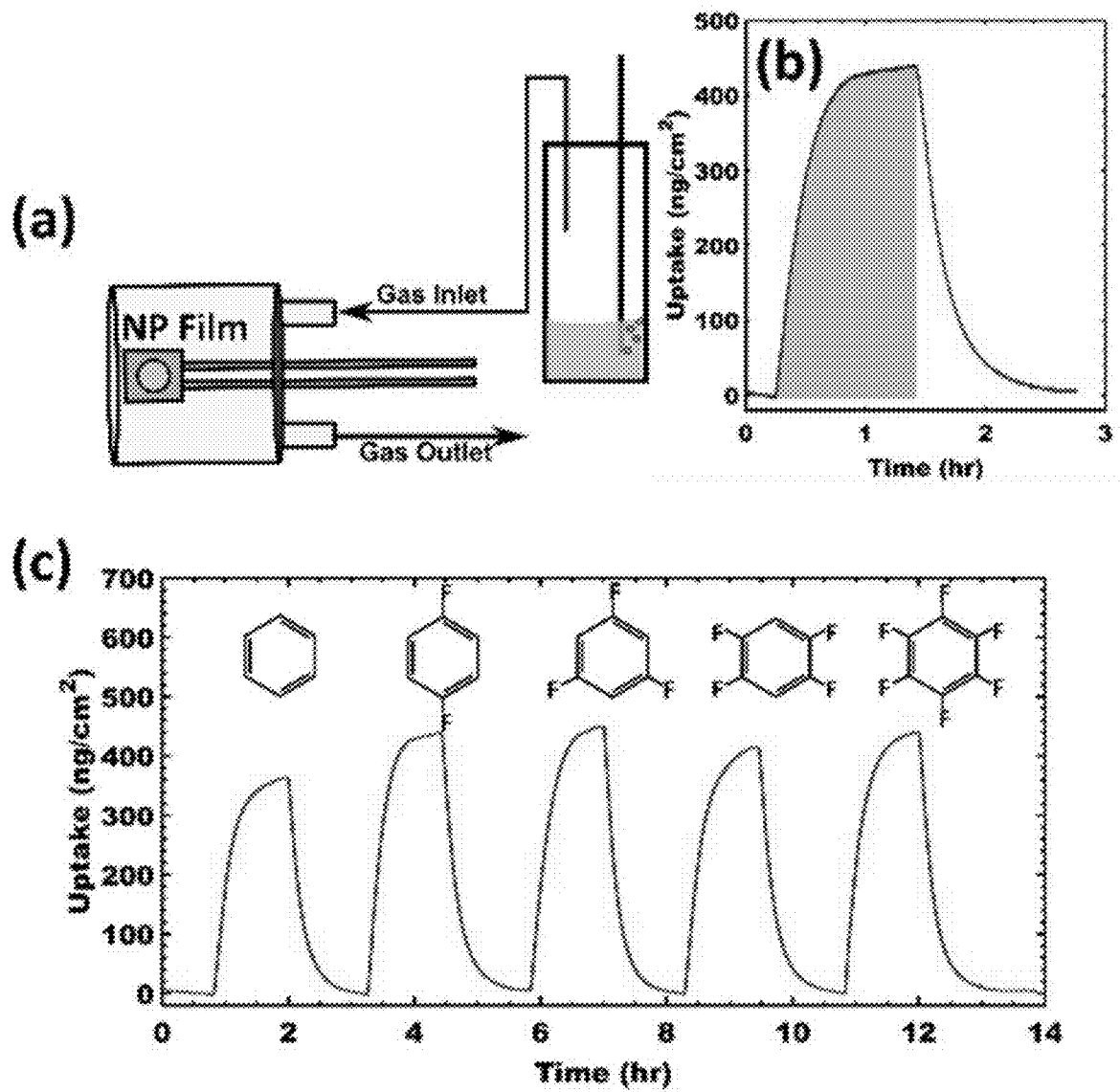
FIG. 7 shows: (a) Scheme of QCM setup with controlled solvent vapor; (b) A characteristic vapor response curve for the 0F NP film with 1,4-difluorobenzene where the shaded region represented the solvent uptake; (c) A sequential series of solvent measurements for a 0F NP film with benzene, 1,4-difluorobenzene, 1,3,5-trifluorobenzene, 1,2,4,5-tetrafluorobenzene, and hexafluorobenzene vapor, respectively.
Figure 13:
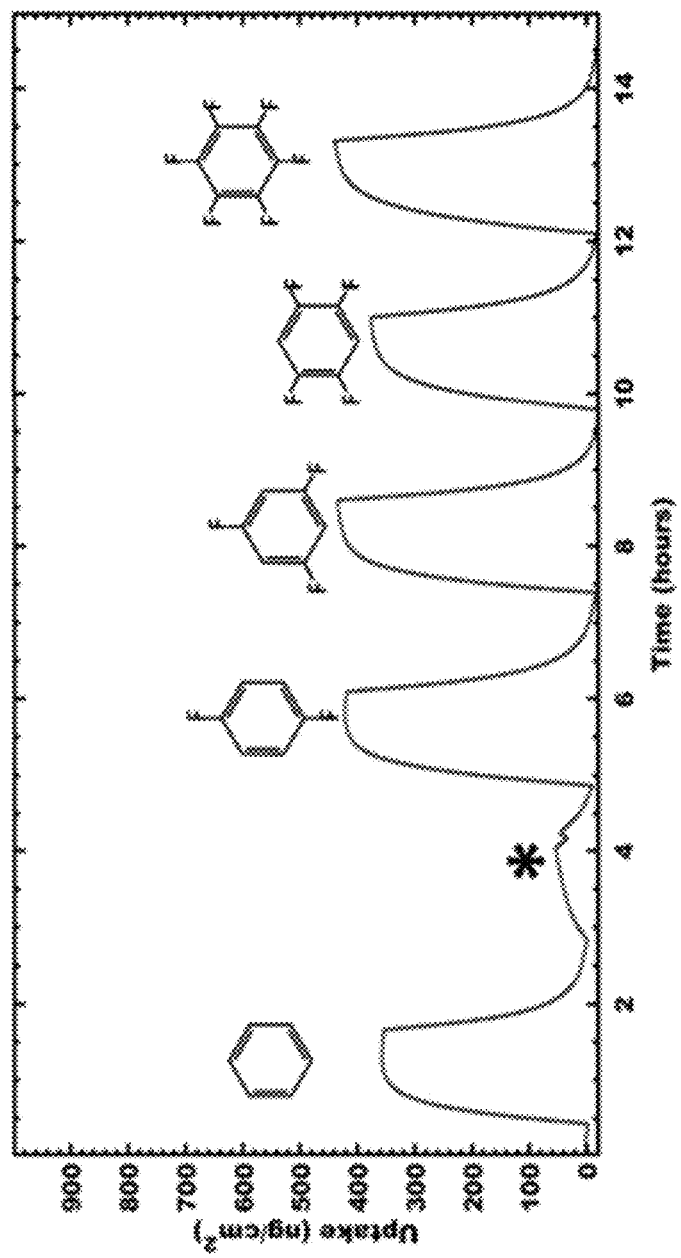
FIG. 13 shows QCM solvent series of the 20F NPs, the asterisk represents the solvent line coming undone during the experiment.
Figure 14:
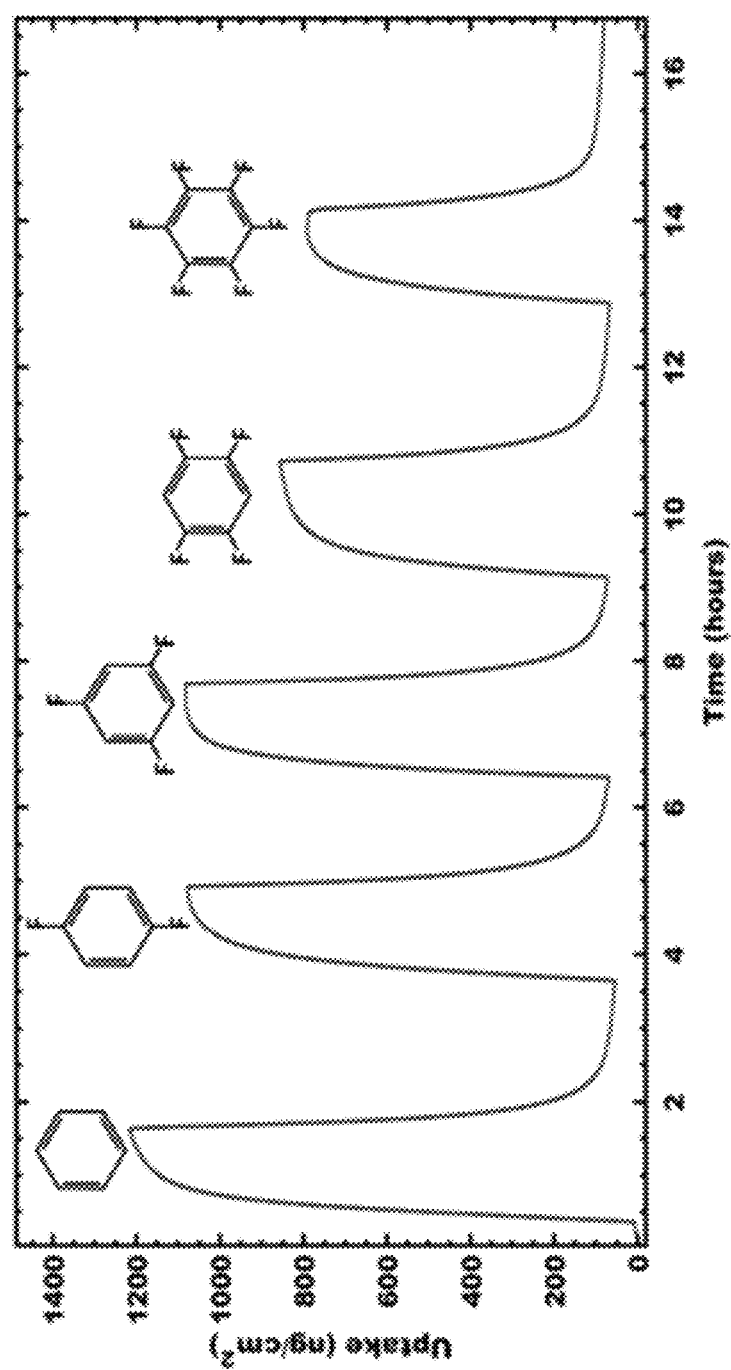
FIG. 14 shows QCM solvent series of the 31F NPs.
Figure 15:
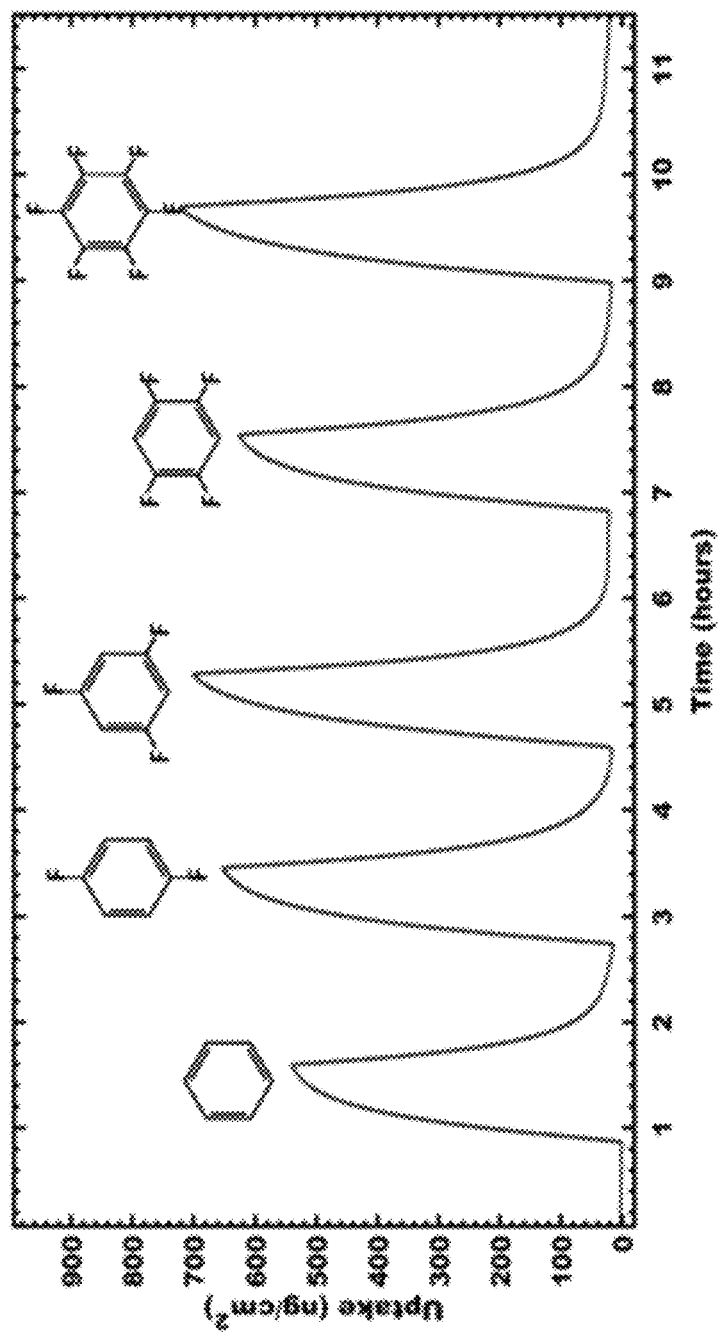
FIG. 15 shows QCM solvent series of the 39F NPs.
Figure 16:
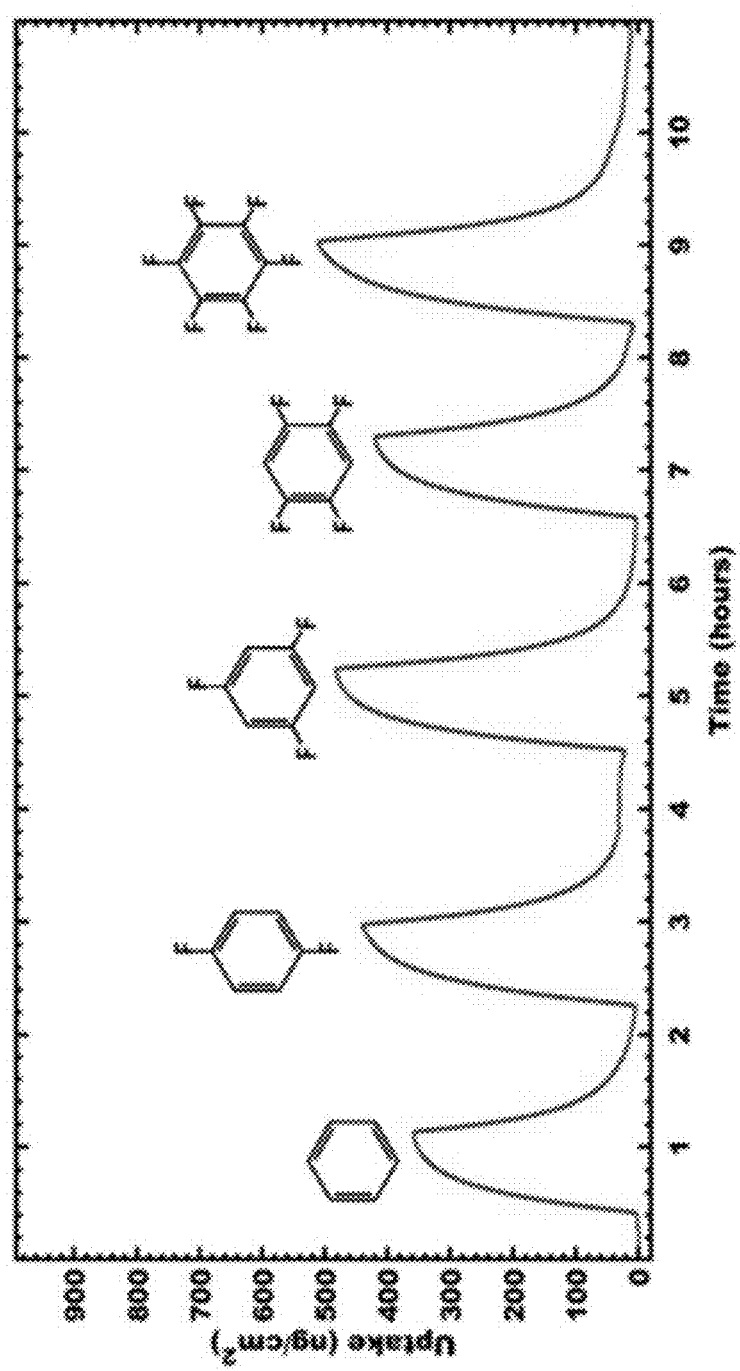
FIG. 16 shows QCM solvent series of the 52F NPs.
Figure 17:
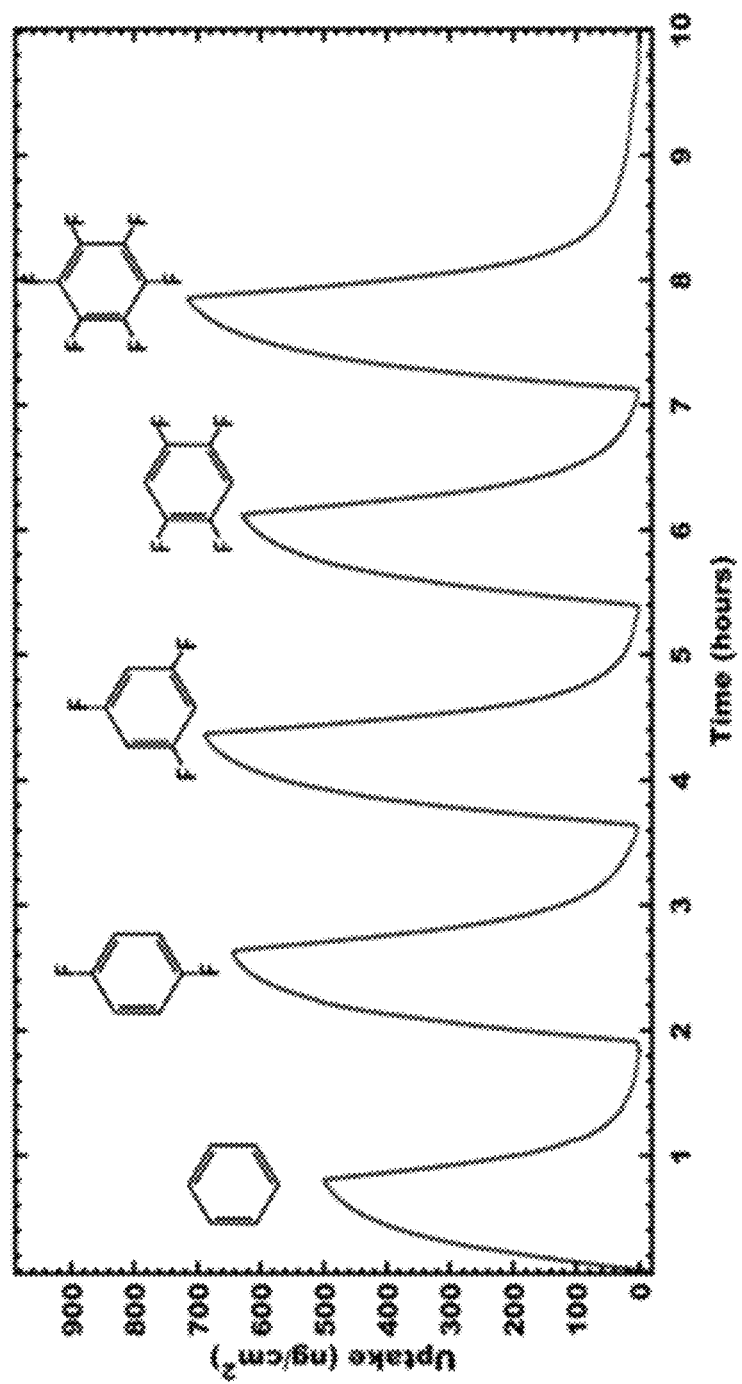
FIG. 17 QCM solvent series of the 39F NPs. For this series 1.8tau was met and when fit the films were nearly equilibrated. The fitted values were used to calculate the relative uptake.
Figure 18:
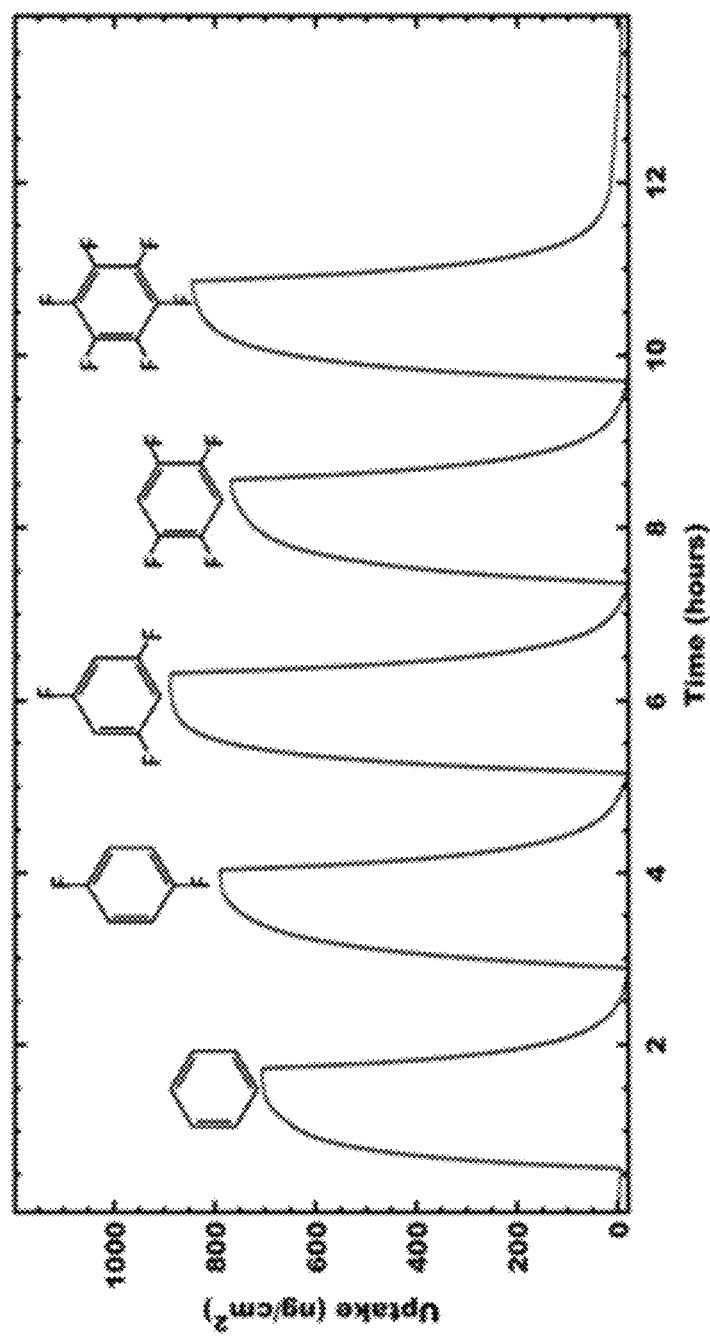
FIG. 18 shows QCM solvent series of the 73F NPs.
Figure 19:
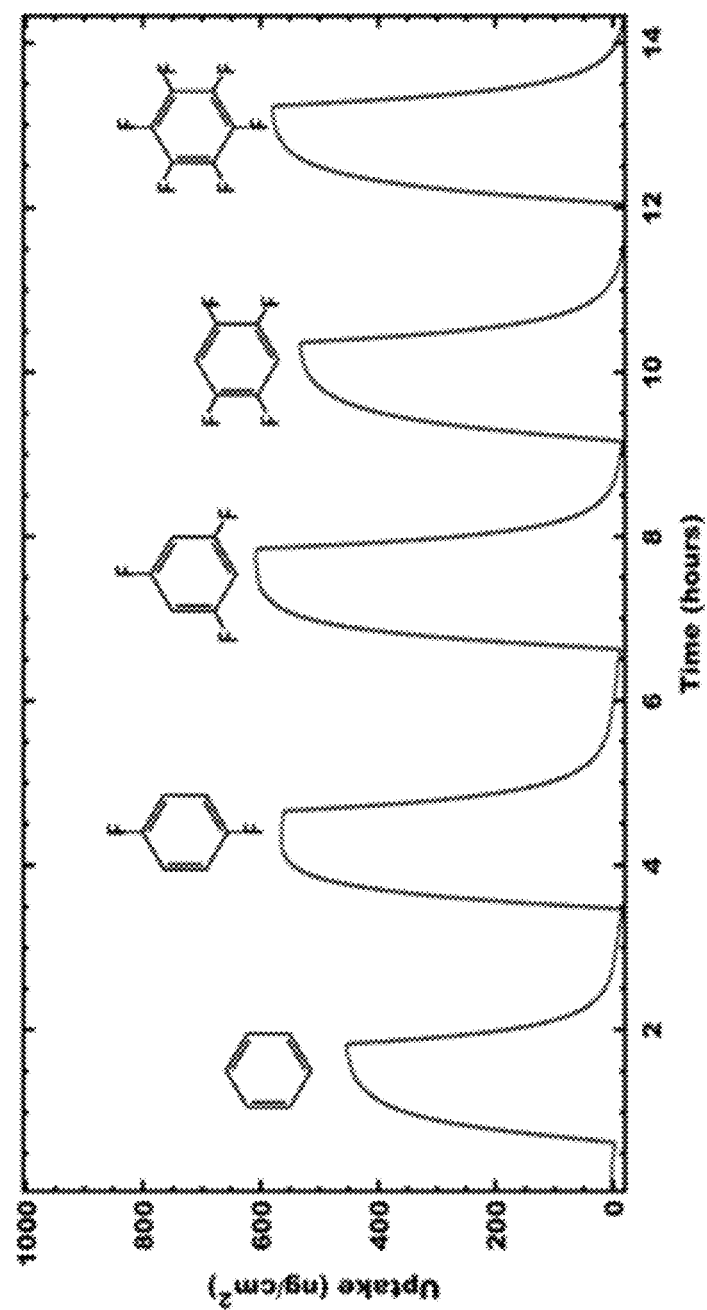
FIG. 19 shows QCM series of the 93F NPs.
Figure 20:
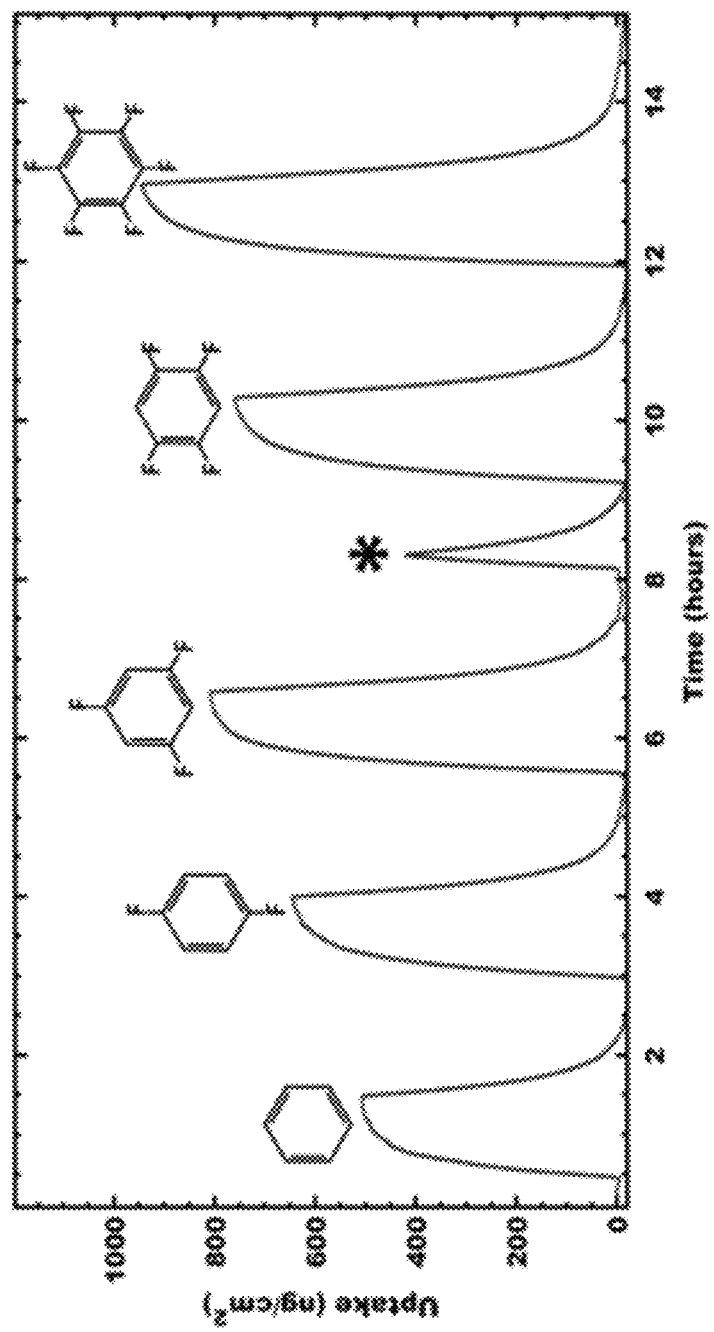
FIG. 20 shows QCM series of the 100F NPs.

A typical uptake experiment is shown in FIG. 7*b*. Comparison of the molecule mass uptake to that of the NP-film thus quantifies the relative extent of uptake. The experiment is easily extendable by examining multiple molecule vapors sequentially, see FIG. 7*c*. (FIG. 7 shows: (a) scheme of QCM setup with controlled solvent vapor; (b) a characteristic vapor response curve for the 0F NP film with 1,4-Difluorobenzene where the shaded region represented the solvent uptake; (c) a sequential series of solvent measurements for a 0F NP film with benzene, 1,4-difluorobenzene, 1,3,5-trifluorobenzene, 1,2,4,5-tetrafluorobenzene, and hexafluorobenzene vapor, respectively.) Typical experiments yielded 10-35% molecule mass uptake relative to the film mass. The complete vapor series for each particle composition can be found in the supplementary information, see FIGS. 13-20. FIG. 13 shows QCM solvent series of the 20F NPs, the asterisk represents the solvent line coming undone during the experiment. FIG. 14 shows QCM solvent series of the 31F NPs. FIG. 15 shows QCM solvent series of the 39F NPs. For this series 1.8tau was met and when fit the films were nearly equilibrated. The fitted values were used to calculate the relative uptake. FIG. 16 shows QCM solvent series of the 52F NPs. FIG. 17 shows QCM solvent series of the 39F NPs. For this series 1.8tau was met and when fit the films were nearly equilibrated. The fitted values were used to calculate the relative uptake. FIG. 18 shows QCM solvent series of the 73F NPs. FIG. 19 shows QCM series of the 93F NPs. FIG. 20 shows QCM series of the 100F NPs. The asterisk denotes the solvent line coming undone. The effect of ligand morphology on molecular uptake are presented next by comparison of the QCM response of NPs with different mixed ligand compositions.

Correlation of Ligand Morphology to molecule-NP Interactions

The simplest approach for series comparisons of molecule-NP interactions is with variable NP and constant molecule vapor. This eliminates the need to quantify and vary the vapor pressure for direct molecule comparisons. Slight variations in composition of mixed ligand NPs can translate into significant macroscopic effects where NPs can become more soluble in a perceived non-solvent or vice versa. Such non-monotonic behavior is typically quantified for NPs with solution saturation experiments. A distinct benefit of the current disclosure's QCM method is the quantification of molecule-NP interactions for non-solvents. The systematic series of mixed ligand NPs prepared above are ideal candidates for the development and testing of this new QCM based approach to probe for non-monotonic trends in molecule-NP interactions with changes to the ligand composition and thus ligand morphology. The current disclosure's synthesis strategy notably eliminates the nanoparticle size distribution as a variable by using a ligand exchange strategy. Recent experimental and computational work coupled with the current disclosure's $^{19}$F NMR measurements suggest a sequence of patchy and stripe-like morphologies here.

Figure 8:
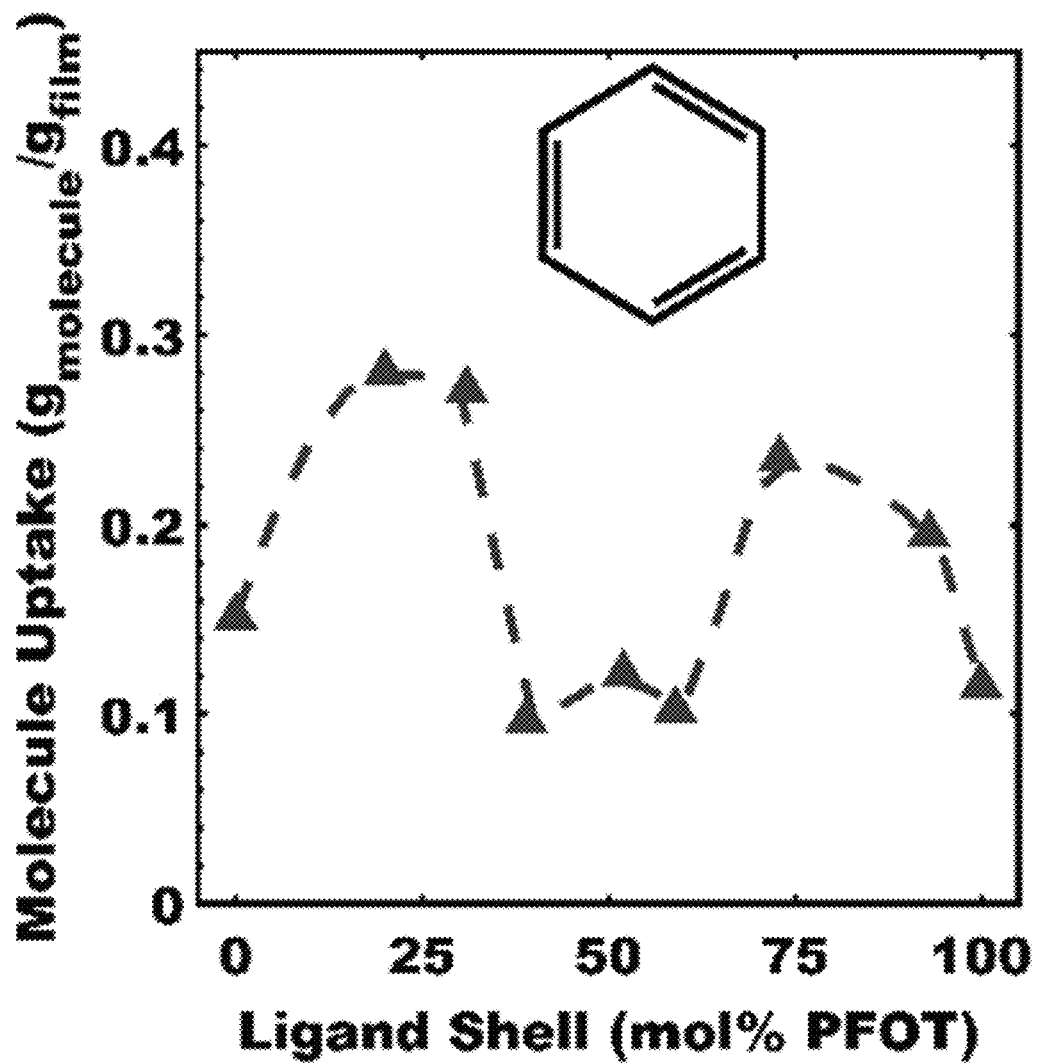
FIG. 8 shows mass uptake of benzene vapor in NP films as a function of PFOT:DDT mixed ligand shell composition.

First, the uptake of benzene vapor was systematically examined using a range of NP surface compositions, see FIG. 8, which shows mass uptake of benzene vapor in NP films as a function of PFOT:DDT mixed ligand shell composition. NPs with only DDT ligands uptook 15 wt % benzene mass and NPs with only PFOT ligands uptook 11% benzene mass. These two extreme points constrain the possible trajectories for monotonic behavior trends to be in intermediate to these two values. The NPs used here with stripe-like morphologies (39-59 mol % PFOT) exhibited reduced solvent uptake relative to the two mono-ligand cases, indicative of molecular cavitation. In contrast, the NPs used here with patchy morphologies (both PFOT-poor and PFOT-rich) exhibited markedly enhanced uptake, indicative of molecular confinement. For example, the 20F NPs up took 28 wt % benzene, a ~2× increase relative to the 0F NPs despite the addition of a fluorophile.

Clearly, the molecule-NP interaction is sensitive to the character of the ligand morphology. The current disclosure notes that $^{19}$F NMR of 31F was at a transition between patchy and stripe-like morphologies and was thus excluded from discussion of generalized trends due to ambiguity. The trends in uptake may be attributed to the nominal dimension of the ligand domains, increasing when transitioning from stripe-like to patchy morphologies. Molecular confinement, e.g., within the gaps between the short and tall ligands, requires that the ligand domains accommodate both the molecule functionality and dimensions. This was rationalized with a confinement argument in a prior study, Rycroft, C. H.; Barenblatt, G. I.; Yamagata, K.; Kondo, T.; Hayashi, S.; Shitamukai, A.; Konno, D.; Matsuzaki, F.; Onami, S.; Nakayama, H.; et al. The Role of Nanostructure in the Wetting Behavior of Mixed-Monolayer-Protected Metal Nanoparticles. Proc. Natl. Acad. Sci. U. S. A. 2008, 110, 6240-6240, which is hereby incorporated by reference, where adding 14 mol % of a solvophobic ligand led to a 30% increased saturation concentration as compared to the mono-ligand NP.

An interesting feature is that even the 100F NPs with mono-ligand PFOT uptook 11 wt % benzene; this interaction of benzene would be missed by solubility measurements alone as the 100F NPs are nearly insoluble in benzene. This marked difference between solubility measurements and QCM solvent uptake exhibit the distinction between molecular uptake and the capability to form a favorable solvation shell. Thus, QCM enables additional insights to quantify molecule-NP interactions independent of solubility.

Figure 9:
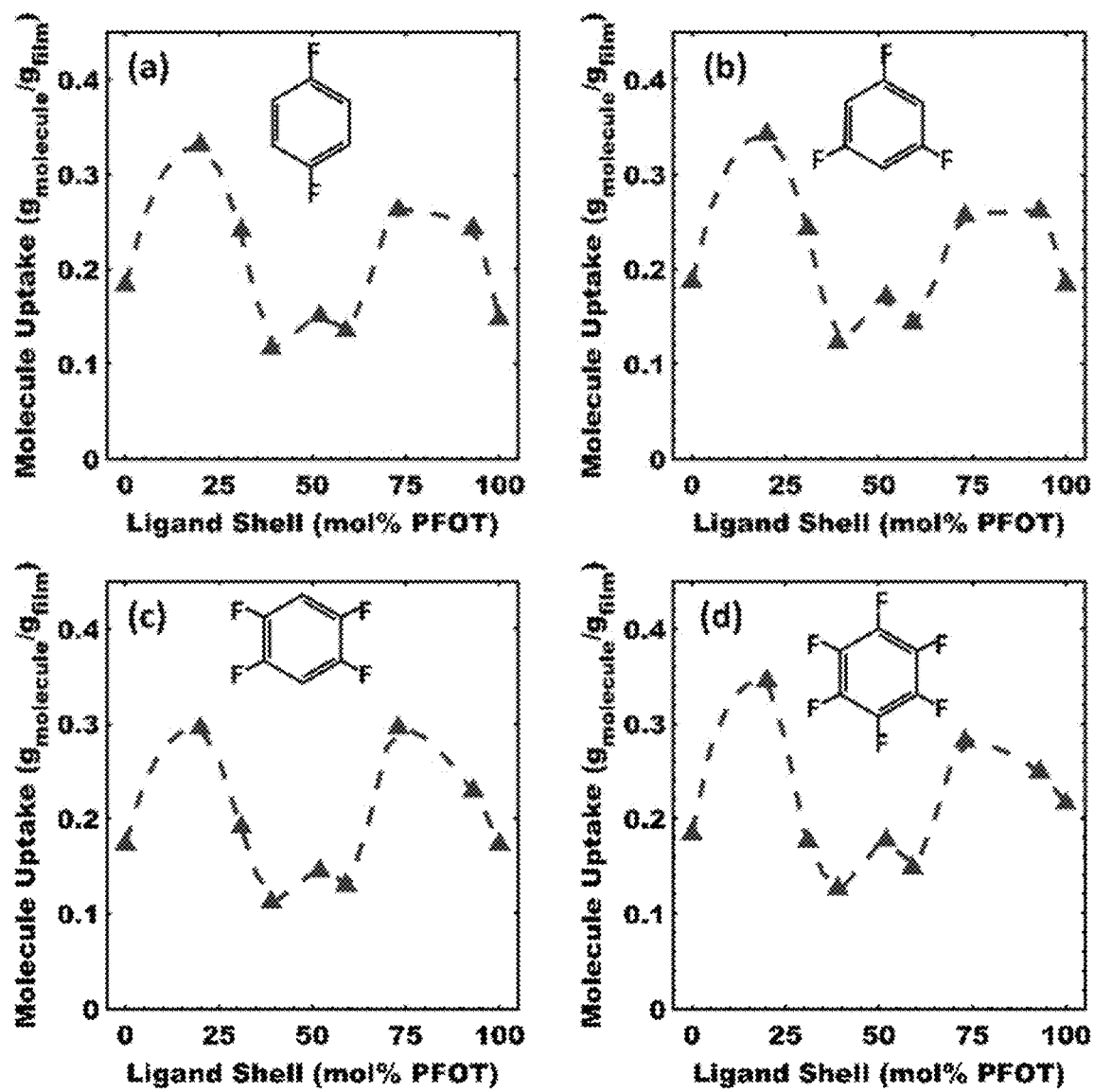
FIG. 9 shows mass uptake of solvent vapors in NP films as a function of PFOT:DDT mixed ligand shell composition: (a) 1,4-difluorobenzene; (b) 1,3,5-trifluorobenzene; (c) 1,2,4,5-tetrafluorobenzene; and (d). Guide lines are indicated with dashes.
Figure 10:
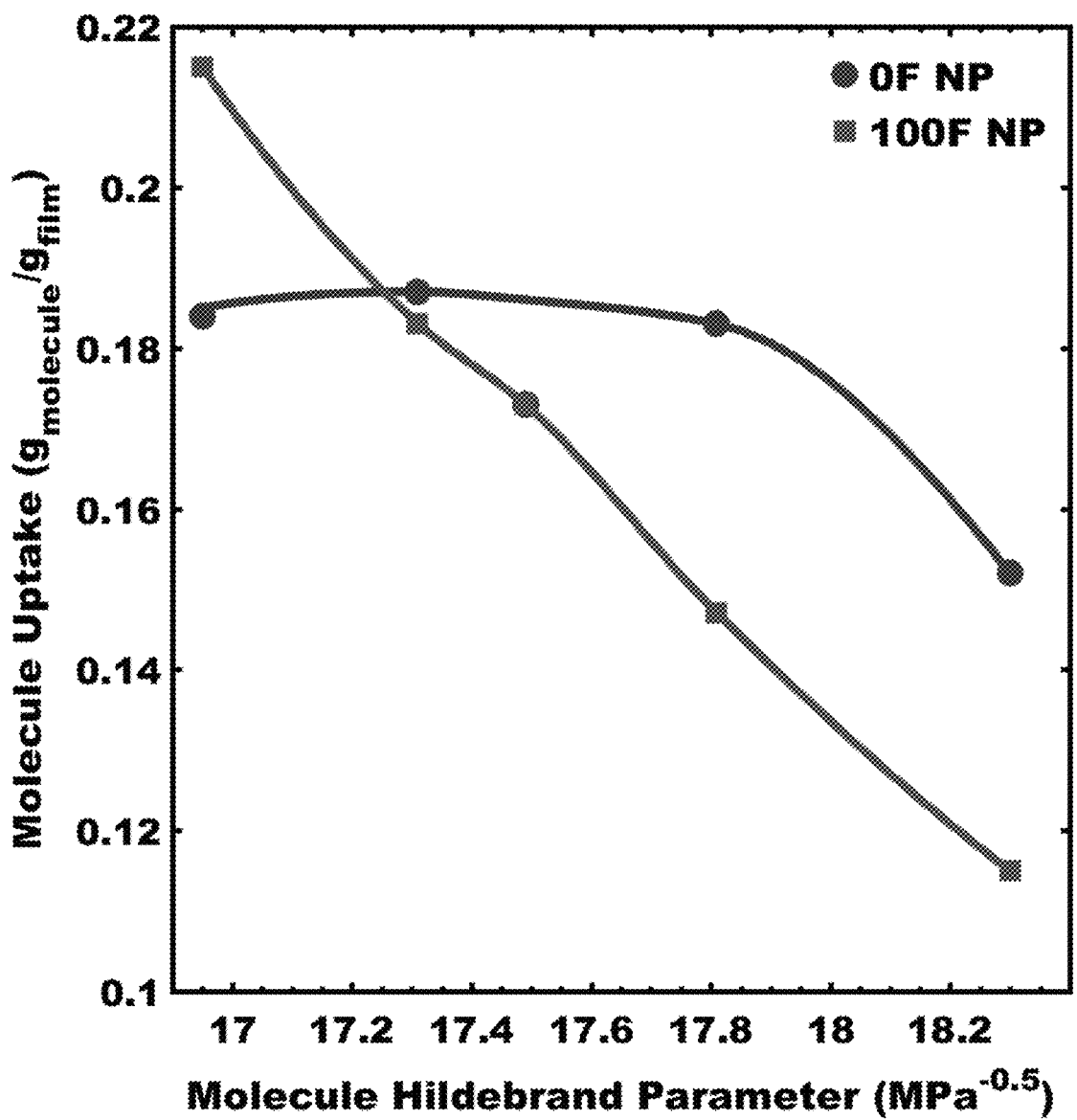
FIG. 10 shows a comparison of different benzene derivative uptakes into the 0F and 100F NP films.

Next a systematic series of benzene derivatives were examined with variable extent of fluorination to determine the effect on overall molecule-NP interactions. The derivatives included 1,4-difluorobenzene, 1,3,5-trifluorobenzene, 1,2,4,5-tetrafluorobenzene, and hexafluorobenzene and were deliberately selected without permanent molecular dipoles. Each solvent was examined across the same series of NP compositions and morphologies as above with benzene, see FIG. 9 and FIG. 21. Analogous behavior to benzene was found in all cases where 1) relative to the mono-ligand cases, the patchy NPs exhibited enhanced uptake corresponding to confinement effects and 2) relative to the mono-ligand cases, the stripe-like NPs exhibited reduced solvent uptake corresponding to cavitation effects. These generalized behaviors for the aromatic molecule series suggests an important role of the relatively constant molecular shape, size, and presence of the aromatic ring. As expected with a like-dissolves-like argument, the 0F 100F NPs exhibited more uptake for highly fluorinated benzene derivatives (low Hildebrand parameter), and vice versa, see FIG. 10. The favorable interaction of PFOT with fluorinated benzene derivatives may be due to either a reduced difference in relative polarizability (dispersion forces) or possibly the presence of weak halogen bonding. Other studies have shown that weakly attractive interactions exist between fluorinated alkanes and electron deficient aromatics. See, Kawahara, S. I.; Tsuzuki, S.; Uchimaru, T. Theoretical Study of the C—F/π Interaction: Attractive Interaction between Fluorinated Alkane and an Electron-Deficient π-System. J. Phys. Chem. A 2004, 108, 6744-6749, and Cavallo, G.; Metrangolo, P.; Milani, R.; Pilati, T.; Priimagi, A.; Resnati, G.; Terraneo, G. The Halogen Bond. Chem. Rev. 2016, 116, 2478-2601, both of which are hereby incorporated by reference.

QCM thus quantifies non-monotonic trends for molecule-NP interactions that are influenced by possible contributions from size/shape, ligand morphology, and chemical nature. The ability to measure these behaviors is crucial to support further investigation, both experimental and computational, into the molecular mechanisms.

Conclusion

A method to quantify mixed ligand shell molecule-NP interactions was developed that is independent of solvation criteria. A QCM apparatus was used to measure the vapor phase uptake of molecules into solid NP thin films. A series of mixed ligand NPs with constant size and variable PFOT/DDT composition were prepared and were confirmed by $^{19}$F NMR to have a range of ligand shell morphologies. The NPs uptake was measured with a systematic series of fluorinated benzene derivatives. The relative mass uptake was non-monotonic with NP ligand shell composition in all cases. For the cases examined, patchy ligand morphologies were found to exhibit more molecule uptake than either stripe-like or the analogous mono-ligand NPs. This enhanced uptake was attributed to confinement effects. In contrast, stripe-like morphologies exhibited decreased molecule uptake relative to the mono-ligand NPs, consistent with cavitation effects. These results highlight the role of ligand shell morphology on molecule-NP interactions. Notably the technique enabled measurements with non-solvents. The ability to measure interactions without a solvation shell leads to a more complete understanding of molecule-NP interactions.

Experimental Methods: Materials

Gold trichloride (99.9%) was obtained from Strem Chemical and stored under inert atmosphere. α,α,α-Trifluorotoluene (≥99%, TFT) and anhydrous iodine lumps (99.99%, under argon) were obtained from BeanTown Chemical. Tetrabutylammonium borohydride (≥98%) and didodecyldimethylammonium borohydride (≥98%) were purchased from TCI America and stored under argon atmosphere before use. Potassium thioacetate (98%), benzene (99%), and 1-dodecane thiol (98%, DDT) were obtained from Alfa Aesar and used as received. 1H, 1H, 2H, 2H-Perfluoro-1-iodooctane iodide (>95%) and 1,3,5-trifluorobenzene (97%) were obtained from Matrix Scientific and used as received. Hexafluorobenzene (97%), 1,2,4,5-tetrafluorobenzene, and 1,4-difluorobenzene were obtained from Oakwood Chemical and used as received. Chloroform-D (99.8%) and benzene-D6 were purchased from Cambridge Isotope Laboratories Inc. and used as received. Toluene (≥99.5%) obtained from Fisher Chemical was subjected to four cycles of freeze-pump-thaw and dried over molecular sieves prior to use.

1H,1H,2H,2H-Perfluoro-1-octanethiol (PFOT) Synthesis

In a round bottom flask, potassium thioacetate was combined with 2-(perfluorohexyl)ethyl iodide in a 1.1:1 molar ratio along with THF. A condenser was connected to the flask and the reaction vessel was sealed and subjected to three cycles of freeze-pump-thaw to remove excess oxygen. It was then filled with inert nitrogen gas and heated for 5 hr at 50° C. The product was collected through filtration and the excess THF was removed by evaporation. The crude 1H,1H,2H,2H-perfluorooctyl thioacetate was purified through vacuum distillation at 70° C., purity and structure was verified with 1H NMR spectroscopy. To obtain the deprotected thiol the purified thioacetate was added to a flask charged with 90 mL of ethanol and 40 mL of concentrated hydrochloric acid. A condenser was connected to the flask and the reaction vessel was sealed and subjected to three cycles of freeze-pump-thaw to remove dissolved oxygen. The vessel was filled with inert nitrogen gas and the reaction was heated for 13 hours at 90° C. The crude thiol was extracted three times with 100 mL of hexanes and washed with 100 mL of deionized water and then dried overnight with magnesium sulfate. The magnesium sulfate was removed through filtration and the excess hexanes was removed through evaporation before the crude thiol was purified through vacuum distillation. The final purity and structure was verified using $^1$H NMR spectroscopy.

Amine-Stabilized NP (Am. NP) Synthesis

In an inert argon glovebox atmosphere, 90 mg of gold(III) chloride was combined with a 0.1 M didodecyldimethylammonium bromide (DDAB) in toluene surfactant solution in a 125 mL Erlenmeyer flask. The solution was gently stirred until the precursor dissolved turning the solution a dark orange color. To this solution 216 μL of dodecylamine was added while stirring, it was then stirred until the dark orange color turned to a light-yellow. In a separate vessel 300 mg of tetra-n-butylammonium bromide (TBAB) was dissolved in 12 mL of the 0.1 M DDAB stock solution, the TBAB solution was then placed in a syringe. Both the flask and syringe were sealed under argon and taken out of the inert atmosphere. The gold precursor solution was then stirred at 1,500 rpm. Once the solution reached 1,500 rpm the TBAB solution was injected into the stirring flask, it immediately changed from a light-yellow color to a deep red. The resulting Am. NP solution was immediately used for ligand displacement.

Ligand Displacement Procedure

A premade ligand solution containing the desired ratio of DDT/PFOT was injected/added to the Am. NPs immediately after synthesis. For mixed ligand NPs, the premade ligand solution was kept at a 1:1 total thiol:gold molar ratio and the proportion of each ligand in the solution was adjusted based on the desired shell composition. Post injection, the AuNPs were stirred for fifteen minutes at room temperature and then boiled at 120° C. for 20 min for the thiols to displace the dodecylamine ligands. Post boiling, the NPs were immediately washed six times using four toluene washes and two α,α,α-trifluorotoluene (TFT) washes to remove excess surfactant and excess ligands. After the washing cycles were complete, the particles were collected by centrifugation from methanol and stored as a powder. The resulting NP batches were termed xF according to the final ligand shell composition, vide infra, where the NPs had x mol % PFOT.

NMR Experiments $^1$H NMR experiments were carried out on a Bruker Avance III-HD 300 MHz. $^{19}$F experiments were carried out on a Bruker Avance III-HD 400A MHz NMR. The $^1$H chemical shifts are referenced to deuterated chloroform, while $^{19}$F chemical shifts are referenced to TFT. An external reference of $CFCl_3$ was used to shift-correct the $^{19}$F spectra to ensure correct peak positioning.

NP purity was analyzed using $^1$H NMR to determine the presence of excess surfactant and unreacted ligand. A typical procedure involved dissolving 5 mg of NPs in either deuterated chloroform or TFT for the heavily fluorinated particles using ultrasonic agitation. The composition of NP ligand shell was measured after ligand stripping using $I_2$ decomposition. Here, 5 mg of NPs were dissolved in deuterated chloroform before 1-3 mg of metallic iodine was added. The solution was gently mixed at 250 rpm using a shaker until complete dissolution of the iodine occurred. It was then allowed to sit overnight to ensure complete disulfide formation. The black precipitate and iodine was removed, and the disulfides were measured using 128 scans on the 1H NMR. The ligand morphology was determined using $^{19}$F NMR measurements with 5 mg of NPs were dissolved in a mixture of $TFT/C_6D_6$ (97/3 wt %). The particles were dispersed with a bath sonicator and were scanned using a 100 ppm window centered at −100 ppm with 256 scans.

Small-Angle X-ray Scattering (SAXS)

X-ray experiments were conducted using a SAXSLAB Ganesha at the South Carolina SAXS Collaborative. A Xenocs GeniX3D microfocus source was used with a Cu target to generate a monochromated beam with a 0.154 nm wavelength. The instrument was calibrated using National Institute of Standards and Technology (NIST) reference material 640c silicon powder with the peak position at 2θ 28.44 where 2θ is the total scattering angle. A Pilatus 300 K detector (Dectris) was used to collect the two-dimensional (2D) scattering patterns. Solutions were prepared by diluting the NPs to ~1 wt. % to avoid structure factor contributions. NP solutions were measured within sealed glass capillaries. A blank sample consisting of a capillary with only toluene/TFT was measured under the same conditions for background subtraction. SAXS data were acquired for 30 minutes at room temperature with an X-ray flux of 21.4 M photons per second incident upon the sample and a sample-to-detector distance of 425 mm. Data were processed using SAXSGUI and custom MATLAB scripts. The scattering form factor was fitted as a Gaussian number average distribution of hard spheres.

Vapor Swelling Chamber

The vapor chamber was built in-house using a bubbler mounted in a water bath to maintain constant temperature. A dry air line with a flow controller was plumbed into the bubbler to generate vapor at a fixed rate of 27 mL/min. The same flow was also used as a purge line after bypassing the bubbler. The output line was directed into a large temperature-controlled oven set to 35° C. containing a long copper coil to equilibrate the vapor temperature before directing the gas phase into a 0.2 L glass chamber housing the QCM crystal. The exhaust line was plumbed from the glass chamber into a fume hood. Glass and metal connectors were used as much as possible to eliminate diffusive uptake of solvents into plastics.

Quartz Crystal Microbalance Measurements

Quartz crystals with 6 MHz resonance frequency were used. NP films were spin coated at 5,000 rpm from 1 wt % solutions onto QCM crystals. The crystal was then measured using a Colnatec Phoenix head and a Colnatec Eon-LT monitor. RC cut QCM crystals were chosen to minimize temperature effects. Each measurement started with a system purge of dry air at the same flow rate of 27 mL/min followed by vapor exposure until the film reached equilibrium, ranging from 25-50 minutes. Following exposure to each solvent, the crystal was again subjected to a purge to remove physiosorbed solvent and restore the baseline QCM frequency. The changes in QCM resonant frequency were recorded 5 times per second. The frequency decrease corresponding to mass uptake was found to equilibrate with a single exponential decay. All data were measured for at least 1.8 times the fitted time constant (>83% progress towards equilibrium) to yield the equilibrium molecular uptake. The resulting frequency data was analyzed using custom MATLAB R2016b scripts. The changes to QCM resonant frequency were converted to the corresponding mass change using the Z-Match method:

$$\Delta m = \frac{v_q \cdot \rho_q}{2\pi \cdot z \cdot f_1} \cdot \tan^{-1}\left(z \cdot \tan\left(\frac{\pi \cdot (f_0 - f_1)}{f_0}\right)\right) = \frac{g}{cm^2} \quad (1)$$

where $\Delta_m$ is the change in mass (g/cm2), uq is the frequency constant (333,600 cm/sec), $p_q$ is the density of quartz (2.648 gm/cm), Z is the Z-factor (1 for mass loadings less than 10-20% frequency shift), $f_1$ is the final resonant frequency, and $f_0$ is the initial resonant frequency. The NP-film mass (g/cm2) was determined by using the resonant frequency of the bare QCM as f0 and the resonant frequency with the NP-film as $f_1$. The molecular mass uptake (g/cm2) was determined similarly by using the resonant frequency of the NP-film as f0 and the resonant frequency with the NP-film under saturated vapor as $f_1$.

Calculation of Solvent-NP Interaction

The molecule-NP interaction was compared for each solvent as a function of the NP ligand shell. The molecular uptake for each film was normalized by the NP film mass to yield comparable relative extents of uptake. The ratio of $(g_{molecule}/cm^2)/(g_{film}/cm^2)$ yielded $g_{molecule}/g_{film}$. The vapor pressure was maintained constant for each solvent since the molecular uptake mass ($g_{molecule}$) is dependent upon vapor pressure.

Ligand Surface Density Calculations

The ligand surface density for NPs was determined using a combination of UV-Vis and quantitative $^1$H NMR. The concentration of the gold NPs was analyzed using a Shimadzu UV-2450 Spectrometer over an absorbance range of 600 to 400 nm. Samples were prepared at approximately 0.2 mg of NPs per 1 mL solvent and placed in a fused quartz glass cuvette with a 1 cm path length. The concentration was calculated using Lambert-Beer law using the absorbance at 508 nm and the extinction coefficient based on the known NP diameter. The extinction coefficients were calculated using the constants k (3.32111) and a (10.80505).

The ligand concentration was quantified after iodine decomposition using $^1$NMR spectroscopy with an internal standard of known concentration. Here the ratio of the internal standard (1,4-Difluorobenzene) to the ratio of the α H1 peaks of each ligand were used to quantify the concentration of each ligand as detailed elsewhere, see Smith, A. M.; Johnston, K. A.; Crawford, S. E.; Marbella, L. E.; Millstone, J. E. Ligand Density Quantification on Colloidal Inorganic Nanoparticles. Analyst 2017, 142, 11-29, which is hereby incorporated by reference. Iodine decomposition was carried out by adding 1-3 mg of metallic iodine to the dispersed NPs, the particles were left to decompose for at least 12 hours to ensure complete disulfide formation leading to a color change from deep red to clear violet. After twelve hours the black precipitate was filtered off and the solution was taken for 1H NMR analysis.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A quartz crystal microbalance method for detecting molecular interactions with nanop articles to quantify molecule-nanoparticle interactions comprising:
   preparing a nanoparticle film on a quartz crystal;
   exposing the nanoparticle film to at least one molecular vapor;
   quantifying mass uptake via analyzing a resonant frequency of the quartz crystal: and
   further comprising eliminating nanoparticle size distribution as a variable via employing ligand exchange.

2. The method of claim 1, further comprising correlating nonmonotonic uptake trends to ligand shell morphologies as a function of confinement and cavitation effects.

3. The method of claim 1, wherein non-solvents, compounds that do not dissolve the nanoparticle film, are used to quantify molecular/nanoparticle interactions.

4. The method of claim 1, wherein a determining morphology of an at least one molecule/nanoparticle shell is accomplished via analyzing nuclear magnetic resonance chemical shifts.

5. The method of claim 4, wherein interfaces of different ligands have a different chemical shift wherein extent of chemical shift is a weighted average of at least one local ligand environment.

6. The method of claim 1, wherein a molecular uptake is measured without requiring a solvation sphere wherein the nanoparticle film is surrounded by a material that acts as a solvent to the nanoparticle film.

7. The method of claim 1, wherein the nanoparticle film is formed by spin coating.

8. The method of claim 1, further comprising comparing molecular mass uptake to nanop article film mass to quantify extent of uptake.

9. The method of clam 1, further comprising probing for non- monotonic trends in molecule-nanop article interactions with changes to ligand composition.

10. A method to quantify mixed ligand shell molecule-nanop article interaction comprising:
    measuring vapor phase uptake of molecules into a solid nanoparticle film, deposited on a crystal, via nuclear magnetic resonance, wherein the nanoparticle film comprises mixed ligand nanoparticles with constant size and variable composition;
    wherein the method is independent of solvation criteria wherein measurements are conducted with the solid nanoparticle film surrounded by solvent; and
    comprising eliminating nanop article size distribution as a variable via employing ligand exchange.

11. The method of claim 10, wherein the crystal is quartz.

12. The method of claim 10, wherein patchy ligand morphologies exhibit more molecule uptake than either stripe-like or mono-ligand nanoparticles.

13. The method of claim 10, wherein measurements occur without requiring a solvation shell wherein the solid nanoparticle film is surrounded by a material that acts as a solvent to the nanoparticle film.

14. The method of claim 10, wherein ligand stripping removing at least one ligand from the solid nanop article film prior to measuring vapor phase uptake is employed.

15. A quartz crystal microbalance method for detecting molecular interactions with nanoparticles to quantify molecule-nanoparticle interactions comprising:

preparing a nanoparticle film on a quartz crystal;
exposing the nanoparticle film to at least one molecular vapor; and
quantifying mass uptake via analyzing a resonant frequency of the quartz crystal; and
wherein ligand stripping is employed.

\* \* \* \* \*

UNITED STATES PATENT AND TRADEMARK OFFICE
CERTIFICATE OF CORRECTION

| | |
|---|---|
| PATENT NO. | : 11,555,815 B2 |
| APPLICATION NO. | : 16/784317 |
| DATED | : January 17, 2023 |
| INVENTOR(S) | : Morgan Stefik et al. |

It is certified that error appears in the above-identified patent and that said Letters Patent is hereby corrected as shown below:

In the Claims

In Column 14, Claim 1, Line 3, "with nanop articles" should read --with nanoparticles--

In Column 14, Claim 8, Line 35, "to nanop article film mass" should read --to nanoparticle film mass--

In Column 14, Claim 9, Line 38, "molecule-nanop article" should read --molecule-nanoparticle--

In Column 14, Claim 10, Lines 40-41, "molecule-nanop article" should read --molecule-nanoparticle--

In Column 14, Claim 14, Line 63, "the solid nanop article film" should read --the solid nanoparticle film--

Signed and Sealed this
Eleventh Day of April, 2023

Katherine Kelly Vidal
*Director of the United States Patent and Trademark Office*